(12) United States Patent
Alekshun et al.

(10) Patent No.: US 8,440,646 B1
(45) Date of Patent: May 14, 2013

(54) **SUBSTITUTED TETRACYCLINE COMPOUNDS FOR TREATMENT OF *BACILLUS ANTHRACIS* INFECTIONS**

(75) Inventors: Michael N. Alekshun, Marlboro, NJ (US); S. Ken Tanaka, Needham, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 1207 days.

(21) Appl. No.: 11/870,317

(22) Filed: Oct. 10, 2007

Related U.S. Application Data

(60) Provisional application No. 60/851,211, filed on Oct. 11, 2006.

(51) Int. Cl.
*A61K 31/65* (2006.01)
(52) U.S. Cl.
USPC .......................................................... 514/152
(58) Field of Classification Search .................. None
See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 2,997,471 A | 8/1961 | Cheney et al. | |
| 3,047,617 A | 7/1962 | Blackwood et al. | |
| 3,062,717 A | 11/1962 | Hammer | |
| 3,159,675 A | 12/1964 | Esse et al. | |
| 3,165,531 A | 1/1965 | Nelson et al. | |
| 3,183,267 A | 5/1965 | Balckwood et al. | |
| 3,345,370 A | 10/1967 | Esse et al. | |
| 3,454,697 A | 7/1969 | Joyner et al. | |
| 3,557,280 A | 1/1971 | Weber et al. | |
| 3,609,188 A | 9/1971 | Esse et al. | |
| 3,622,627 A | 11/1971 | Blackwood et al. | |
| 3,674,859 A | 7/1972 | Beutel et al. | |
| 3,824,285 A | 7/1974 | Blackwood et al. | |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 5,498,699 A | 3/1996 | Djokic et al. | |
| 6,043,231 A | 3/2000 | Pruzanski et al. | |
| 6,500,812 B2 | 12/2002 | Nelson et al. | |
| 6,506,740 B1 | 1/2003 | Ashley et al. | |
| 6,613,756 B2 | 9/2003 | Duncan et al. | |
| 6,617,318 B1 | 9/2003 | Nelson et al. | |
| 6,624,168 B2 | 9/2003 | Nelson et al. | |
| 6,638,922 B2 | 10/2003 | Ashley et al. | |
| 6,642,270 B2 | 11/2003 | Nelson et al. | |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,833,365 B2 | 12/2004 | Levy et al. | |
| 6,841,546 B2 | 1/2005 | Draper et al. | |
| 6,846,939 B2 | 1/2005 | Nelson et al. | |
| 6,849,615 B2 | 2/2005 | Nelson et al. | |
| 6,894,036 B2 | 5/2005 | Ashley et al. | |
| 6,946,453 B2 | 9/2005 | Ashley et al. | |
| 7,001,918 B2 | 2/2006 | Huss et al. | |
| 7,045,507 B2 | 5/2006 | Draper et al. | |
| 7,056,902 B2 | 6/2006 | Nelson et al. | |
| 7,067,681 B2 | 6/2006 | Nelson et al. | |
| 7,075,582 B2 | 7/2006 | Alekshun et al. | |
| 2002/0022608 A1 | 2/2002 | Duncan et al. | |
| 2002/0123637 A1 | 9/2002 | Levy et al. | |
| 2002/0128237 A1 | 9/2002 | Nelson et al. | |
| 2002/0128238 A1 | 9/2002 | Nelson et al. | |
| 2002/0132798 A1 | 9/2002 | Nelson et al. | |
| 2002/0160987 A1 | 10/2002 | Ashley et al. | |
| 2003/0055025 A1 | 3/2003 | Nelson et al. | |
| 2003/0125348 A1 | 7/2003 | Nelson et al. | |
| 2003/0166952 A1 | 9/2003 | Nelson et al. | |
| 2003/0195174 A1 | 10/2003 | Ashley et al. | |
| 2004/0002481 A1 | 1/2004 | Ashley et al. | |
| 2004/0048835 A1 | 3/2004 | Nelson et al. | |
| 2004/0063674 A1 | 4/2004 | Levy et al. | |
| 2004/0067912 A1 | 4/2004 | Hlavka et al. | |
| 2004/0092490 A1 | 5/2004 | Draper et al. | |
| 2004/0138183 A1 | 7/2004 | Nelson et al. | |
| 2004/0152674 A1 | 8/2004 | Levy et al. | |
| 2004/0176334 A1 | 9/2004 | Nelson et al. | |
| 2004/0214800 A1 | 10/2004 | Levy et al. | |
| 2004/0214801 A1 | 10/2004 | Nelson et al. | |
| 2004/0242548 A1 | 12/2004 | Draper et al. | |
| 2004/0266740 A1 | 12/2004 | Huss et al. | |
| 2005/0020545 A1 | 1/2005 | Draper et al. | |
| 2005/0024549 A1 | 2/2005 | Gotoh et al. | |
| 2005/0026875 A1 | 2/2005 | Nelson et al. | |
| 2005/0026876 A1 | 2/2005 | Nelson et al. | |
| 2005/0038002 A1 | 2/2005 | Nelson et al. | |
| 2005/0070510 A1 | 3/2005 | Draper et al. | |
| 2005/0119235 A1 | 6/2005 | Nelson et al. | |
| 2005/0137174 A1 | 6/2005 | Ohemeng et al. | |
| 2005/0143352 A1 | 6/2005 | Nelson et al. | |

(Continued)

FOREIGN PATENT DOCUMENTS

| | | | |
|---|---|---|---|
| WO | WO-03005971 A2 | | 1/2003 |
| WO | WO-200464728 A2 | | 8/2004 |
| WO | WO 2005/009943 | * | 2/2005 |
| WO | WO-2005009943 A2 | | 2/2005 |
| WO | WO-2005056538 A1 | | 6/2005 |
| WO | WO-2006047671 A2 | | 5/2006 |
| WO | WO-2008079339 A2 | | 7/2008 |

OTHER PUBLICATIONS

Centers for Disease Control and Prevention (Morb Mortal Wkly Rep 50:1014-1016, 2001).*
New York City Dept of Health and Mental Hygiene (available online at www.nyc.gov, Jul. 2000).*
US 6,897,204, 5/24/2005, Hlavka et al. (withdrawn).

*Primary Examiner* — Craig Ricci

(74) *Attorney, Agent, or Firm* — Mintz Levin Cohn Ferris Glovsky and Popeo, P.C.; Heidi A. Erlacher; Yongjun Zhang

(57) ABSTRACT

Methods and compositions for the treatment of *Bacillus anthracis* infections are described.

23 Claims, No Drawings

U.S. PATENT DOCUMENTS

| | | |
|---|---|---|
| 2005/0143353 A1 | 6/2005 | Nelson et al. |
| 2005/0148551 A1 | 7/2005 | Nelson et al. |
| 2005/0187198 A1 | 8/2005 | Nelson et al. |
| 2005/0215532 A1 | 9/2005 | Levy et al. |
| 2005/0250744 A1 | 11/2005 | Levy et al. |
| 2005/0267079 A1 | 12/2005 | Hlavka et al. |
| 2005/0288262 A1 | 12/2005 | Bandarage et al. |
| 2006/0001487 A1 | 1/2006 | Petrovic et al. |
| 2006/0001669 A1 | 1/2006 | Sutardja et al. |
| 2006/0003971 A1 | 1/2006 | Nelson |
| 2006/0008463 A1 | 1/2006 | Itoh et al. |
| 2006/0008467 A1 | 1/2006 | Haynes et al. |
| 2006/0008933 A1 | 1/2006 | Muller et al. |
| 2006/0089336 A1 | 4/2006 | Nelson et al. |

* cited by examiner

SUBSTITUTED TETRACYCLINE COMPOUNDS FOR TREATMENT OF *BACILLUS ANTHRACIS* INFECTIONS

RELATED APPLICATIONS

This application claims priority to U.S. Provisional Patent Application No. 60/851,211, filed on Oct. 11, 2006, the entire contents of which are incorporated herein by reference.

BACKGROUND OF THE INVENTION

In the fall of 2001, letters intentionally contaminated with *Bacillus anthracis* were mailed to individuals in Florida, Washington, D.C., and New York City. These events resulted in exposures both at the sites of delivery and also at sites the letters passed through in New Jersey, Pennsylvania, Virginia, Maryland, and Connecticut. In total, there were 11 cases of documented inhalation anthrax infections, including 5 deaths, and 11 cases of documented cutaneous anthrax infections. Antimicrobial prophylaxis for at least 60 days was recommended for about 10,000 individuals; ultimately, about 32,000 people actually received prophylactic therapy.

The public health crisis in antibiotic resistance generally focuses on nosocomial and community-acquired infections with organisms that have naturally become resistant to multiple agents. This situation has developed due to a combination of antibiotic use (including overuse and misuse) and the emergence of freely transmissible resistance determinant(s). Organisms that might be (or have been) used by bioterrorists could acquire antibiotic resistance not only naturally, but also as a result of intentional manipulation.

Ciprofloxacin, doxycycline, and penicillin G procaine (penicillin) are the three drugs currently approved for intravenous therapy of all forms of anthrax (cutaneous (skin), inhalation, and gastrointestinal) infection. Mobile elements that confer resistance to tetracyclines and penicillins can be introduced into *B. anthracis* and are functional; resistance to ciprofloxacin can be induced by passage in vitro. Thus, there is a real possibility of multiple drug resistant (MDR) anthrax and alternative agents effective against such strains are needed.

SUMMARY OF THE INVENTION

In one embodiment, the invention pertains to novel, narrow-spectrum, orally bioavailable substituted tetracycline compounds that are active against *B. anthracis*, including strains expressing resistance to known tetracycline resistance elements.

In a further embodiment, the invention pertains to a method for treating a *Bacillus anthracis* infection in a subject. The method includes administering to the subject an effective amount of a substituted tetracycline compound, such that the *Bacillus anthracis* infection in the subject is treated.

In another embodiment, the invention also pertains to a pharmaceutical composition comprising an effective amount of a substituted tetracycline compound for the treatment of a *Bacillus anthracis* infection and a pharmaceutically acceptable carrier.

DETAILED DESCRIPTION OF THE INVENTION

In one embodiment, the invention pertains to a method for treating a *Bacillus anthracis* infection in a subject. The method includes administering to the subject an effective amount of a substituted tetracycline compound, such that the *Bacillus anthracis* infection in the subject is treated.

The term "*Bacillus anthracis* infection" includes any state, diseases, or disorders caused or which result from exposure or alleged exposure to *Bacillus anthracis* or another member of the *Bacillus cereus* group of bacteria.

The *Bacillus cereus* group of bacteria is composed of *B. anthracis* (the etiologic agent of anthrax), *B. cereus* and *B. weihenstephanensis* (food borne pathogens), *B. thuringiensis* (an insect pathogen), and *B. mycoides* (non-pathogenic). *B. anthracis* is associated with three different clinical forms of infection. Inhalation anthrax is rare, with only 18 cases reported in the US from 1900-1976 and none from 1976-2001. The mortality rate of inhalation anthrax has been reported to range from 40% to 89%; however, many cases are from the pre-antibiotic era {Inglesby, 2002 #1942}. Patients that died following the accidental dissemination of *B. anthracis* from a bioweapons facility in Sverdlovsk, Russia in 1976 exhibited hemorrhagic thoracic lymphadenitis, hemorrhagic mediastinitis, and pleural effusions. This experience confirmed that typical bronchopneumonia is not a characteristic of pulmonary anthrax.

The most common infection due to *B. anthracis* is cutaneous anthrax, which is rarely fatal when treated with appropriate antibiotics. Gastrointestinal anthrax may develop after eating improperly prepared, contaminated meat; these infections are typically encountered in developing countries in Africa and Asia.

The term "subject" includes animals (e.g., mammals, e.g., cats, dogs, horses, pigs, cows, sheep, rodents, rabbits, squirrels, bears, primates (e.g., chimpanzees, gorillas, and humans)) which are capable of (or currently) suffering from a *Bacillus anthracis* infection. It also includes transgenic animal models.

The term "treated," "treating" or "treatment" includes therapeutic and/or prophylactic treatment of a *Bacillus anthracis* infection. The treatment includes the diminishment or alleviation of at least one symptom associated or caused by a *Bacillus anthracis* infection. For example, treatment can be diminishment of one or several symptoms of a *Bacillus anthracis* infection or complete eradication.

The language "effective amount" of the tetracycline compound is that amount necessary or sufficient to treat or prevent a *Bacillus anthracis* infection in a subject, e.g. prevent the various morphological and somatic symptoms of multiple sclerosis. The effective amount can vary depending on such factors as the size and weight of the subject, the type of illness, or the particular tetracycline compound. For example, the choice of the tetracycline compound can affect what constitutes an "effective amount." One of ordinary skill in the art would be able to study the aforementioned factors and make the determination regarding the effective amount of the tetracycline compound without undue experimentation.

The term "tetracycline compound" does not include minocycline, doxycycline, or tetracycline. The term includes substituted tetracycline compounds or compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

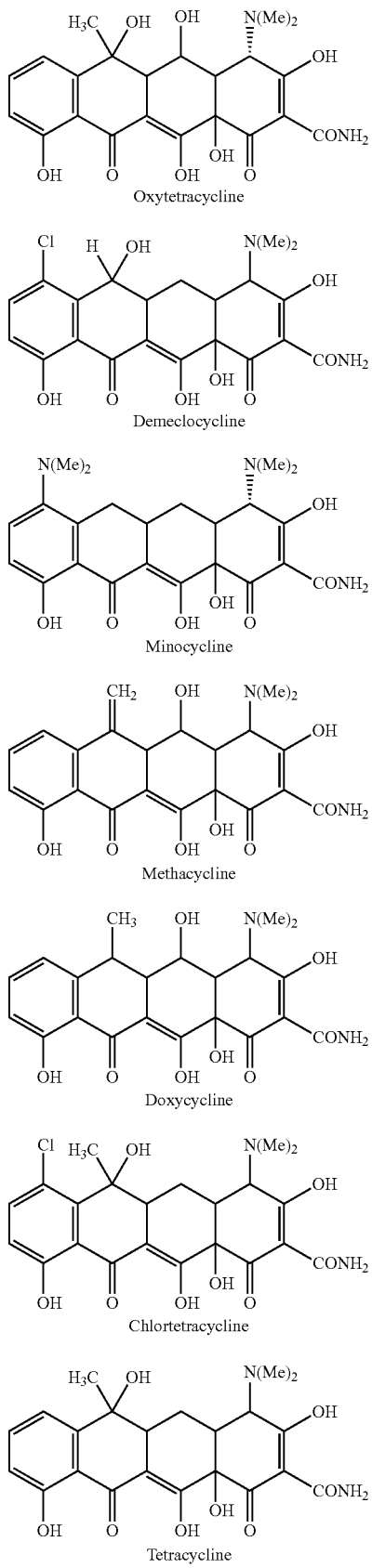

TABLE 1-continued

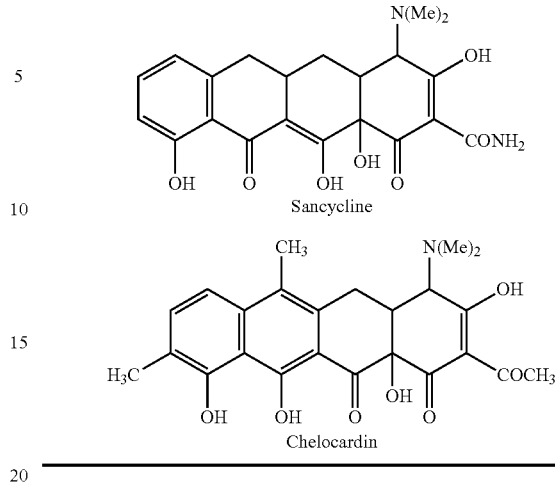

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a Cl-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a,11a dehydro tetracyclines; 11a Cl-6,12 hemiketal tetracyclines; 11a Cl-6-methylene tetracyclines; 6,13 diol tetracyclines; 6-benzylthiomethylene tetracyclines; 7,11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-α acetoxy-6-demethyl tetracyclines; 6-β acetoxy-6-demethyl tetracyclines; 7,13-epithiotetracyclines; oxytetracyclines; pyrazolotetracyclines; 11a halogens of tetracyclines; 12a formyl and other esters of tetracyclines; 5,12a esters of tetracyclines; 10,12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

The term "substituted tetracycline compound" includes tetracycline compounds with one or more additional substituents, e.g., at the 1, 2, 3, 4, 5, 6, 7, 8, 9, 10, 11, 11a, 12, 12a or 13 position or at any other position which allows the substituted tetracycline compound of the invention to perform its intended function, e.g., treat B. anthracis infections.

In a further embodiment, the substituted tetracycline compound has an MIC less than that of doxycycline for at least one strain of Bacillus anthracis. The MIC of the substituted tetracycline compound can be tested using the method described in the Examples. In a further embodiment, the substituted tetracycline compound has an MIC less than 32 μg/ml for a doxycycline resistant strain of Bacillus anthracis. In a further embodiment, the MIC of the substituted tetracycline has an MIC that is 90% or less, 50% or less, 20% or less, 10% or less, 5% or less than the MIC of doxycycline for a particular strain of Bacillus anthracis.

In a further embodiment, the substituted tetracycline compound has an MIC less than that of ciproflaxin for at least one strain of Bacillus anthracis. The MIC of the substituted tetracycline compound can be tested using the method described in the Examples. In a further embodiment, the substituted tetracycline compound has an MIC less than 32 μg/ml for a ciproflaxin resistant strain of Bacillus anthracis. In a further embodiment, the MIC of the substituted tetracycline has an MIC that is 90% or less, 50% or less, 20% or less, 10% or less, 5% or less than the MIC of ciproflaxin for a particular strain of Bacillus anthracis.

In a further embodiment, the substituted tetracycline compound of the invention is of the formula I:

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen, optionally linked to $R^2$ to form a ring;

$R^{2''}$ is cyano or C(=O)—$NR^2R^2$;

$R^2$ is hydrogen, alkyl, halogen, alkenyl, alkynyl, aryl, hydroxyl, thiol, cyano, nitro, acyl, formyl, alkoxy, amino, alkylamino, heterocyclic, or absent, optionally linked to $R^1$ to form a ring;

$R^{2'}$, $R^3$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$, and $R^{12}$ are each independently hydrogen, alkyl, aryl, benzyl, arylalkyl, or a pro-drug moiety;

$R^4$ and $R^{4'}$ are each independently $NR^{4a}R^{4b}$, alkyl, acyl, alkenyl, alkynyl, hydroxyl, halogen, hydrogen, or taken together =N—$OR^{4a}$;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, dialkylamino, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, boronic ester, alkylcarbonyl, thionitroso, or —$(CH_2)_{0-3}(NR^{7c})_{0-1}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}(NR^{8c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}(NR^{9c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^6R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In a further embodiment, $R^{2''}$ is C(=O)$NH_2$; $R^3$, $R^{10}$, $R^{11}$, and $R^{12}$ are each hydrogen or a prodrug moiety; $R^4$ is $NR^{4a}R^{4b}$; $R^{4a}$ and $R^{4b}$ are each methyl; $R^5$ is hydrogen; $R^8$ is hydrogen; X is $CR^6R^{6'}$; $R^6$ is hydrogen; and $R^{5'}$ and $R^{6'}$ are hydrogen.

In another further embodiment, $R^8$ and $R^9$ are hydrogen.

In yet another further embodiment, $R^7$ is substituted phenyl, a boronic ester, alkylcarbonyl, heterocyclic, aminoalkyl, or arylalkynyl. Examples of substituents for phenyl $R^7$ groups include, but are not limited to, alkoxy, alkyl-O—N=C—$CR^{7g}R^{7h}$, alkylaminoalkyl, alkenylaminoalkyl, alkoxyalkylaminoalkyl, substituted alkyl, and substituted carbonylamino, wherein $R^{7g}$ and $R^{9h}$ are each independently hydrogen or alkyl.

In another further embodiment, $R^7$ is substituted or unsubstituted heteroaryl, e.g., substituted or unsubstituted pyrimidinyl, pyridinyl, or furanyl.

In another further embodiment, $R^7$ is substituted or unsubstituted piperidinyl-alkyl. In other embodiments, $R^7$ is pyridinyl-alkynyl or substituted or unsubstituted phenyl-alkynyl.

In other embodiment, $R^7$ is hydrogen and $R^9$ is substituted carbonylamino.

In other embodiments, $R^8$ is hydrogen; $R^7$ is heterocyclic, alkyl, alkyl-O—N=C—$CR^{7g}R^{7h}$, or dimethylamino, wherein $R^{7g}$ and $R^{9h}$ are each independently hydrogen or alkyl.

In a further embodiment, $R^9$ is aminoalkyl. Examples of aminoalkyl $R^9$ moieties include aminomethyl moieties and moieties of the formula:

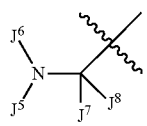

wherein:

$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring; and $J^7$ and $J^8$ are each alkyl, halogen, or hydrogen.

In a further embodiment, $J^7$ and $J^8$ are each hydrogen.

In another further embodiment, $J^6$ is hydrogen and $J^5$ is substituted or unsubstituted alkyl, e.g., methyl, ethyl, propyl, butyl, pentyl, 2-methyl-propyl, hexyl, and/or cyclohexyl. Examples of substituents of $J^5$ include one or more fluorines or substituted or unsubstituted phenyl groups.

In another embodiment, $J^5$ and/or $J^6$ is substituted or unsubstituted alkyl or alkenyl. Examples of $J^5$ and/or $J^6$ include methyl, ethyl, propyl, propenyl, 2-methyl-propyl, butyl, butenyl, pentyl, pentenyl, hexyl, and hexenyl. In a further embodiment, $J^5$ is substituted with one or more fluorines or substituted or unsubstituted phenyl groups.

In another further embodiment, $J^5$ and $J^6$ are linked to form a ring, e.g., a piperidinyl ring or a fused ring, e.g., 2,3-dihydro-indole or an decahydro-isoquinoline. In another further embodiment, the piperidinyl ring is substituted with one or more halogens, one or more heterocyclic groups or one or more halogenated alkyl groups (e.g., trifluoromethyl).

In one embodiment, $R^{2''}$ is $C(=O)NH_2$; $R^{4'}$, $R^{5'}$, $R^3$, $R^{10}$, $R^{11}$, and $R^{12}$ are each hydrogen or a prodrug moiety; $R^4$ is $NR^{4a}R^{4b}$; $R^{4a}$ and $R^{4b}$ are each methyl; $R^5$ is hydroxyl; $R^8$ is hydrogen; X is $CR^6R^{6'}$; $R^6$ is hydrogen and $R^{6'}$ is alkyl (e.g., methyl).

In a further embodiment, $R^7$ is hydrogen and $R^9$ aminoalkyl (e.g., piperidinyl alkyl, such as halogenated alkyl substituted piperidinyl alkyl, for example, trifluoromethyl substituted piperidinylalkyl).

In another embodiment, the substituted tetracycline compound is selected from the group consisting of:

A

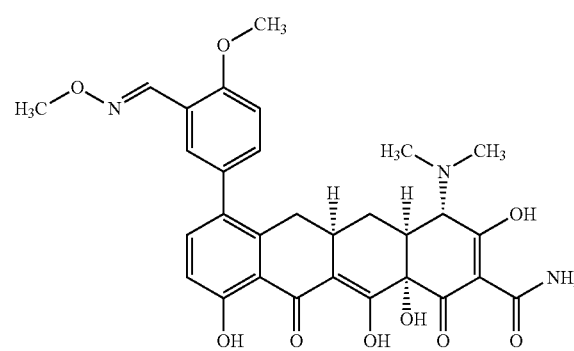

-continued

B

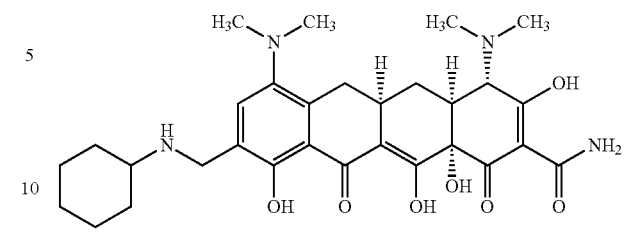

C

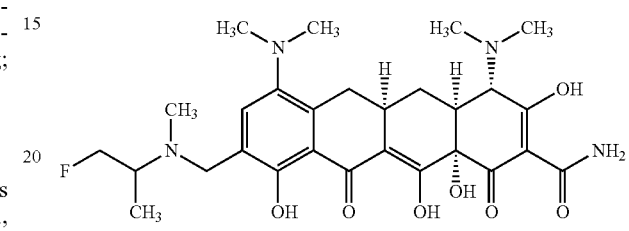

D

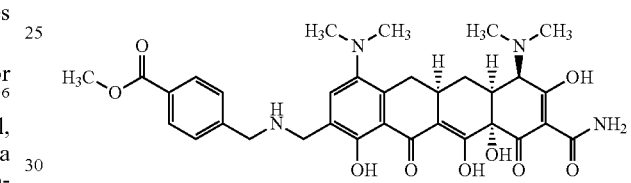

E

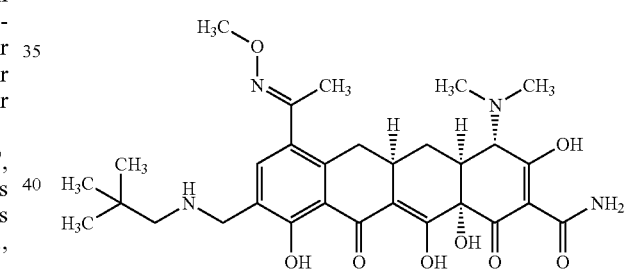

F

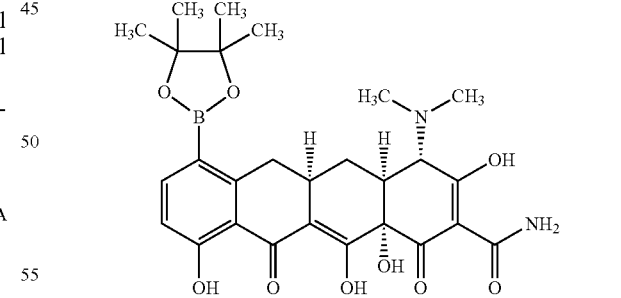

G

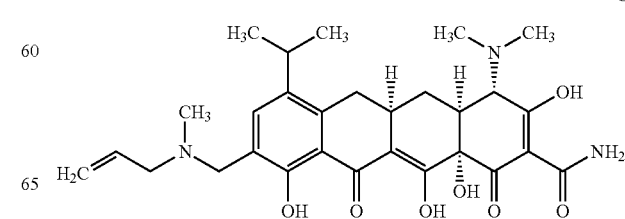

H
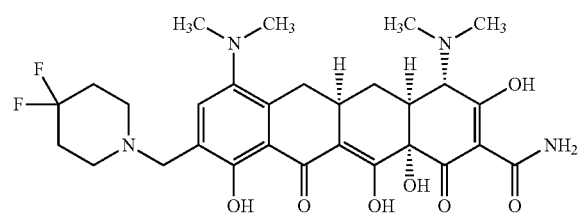
I
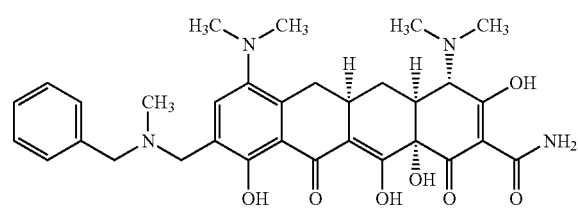
J
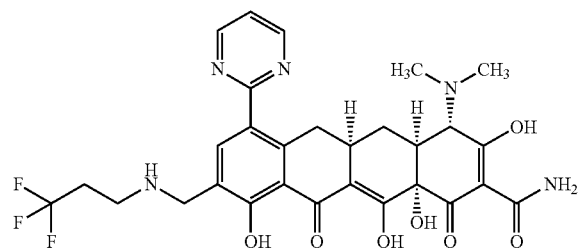
K
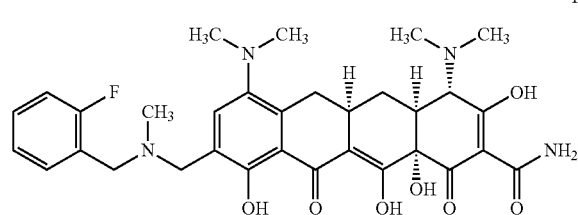
L
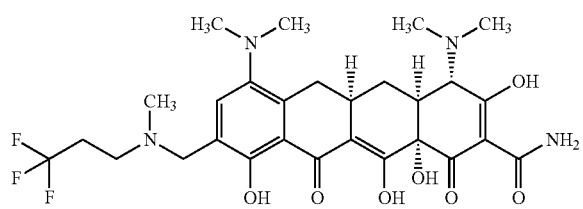
M
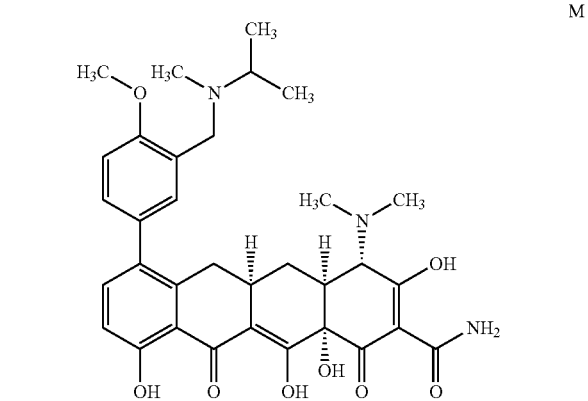
N
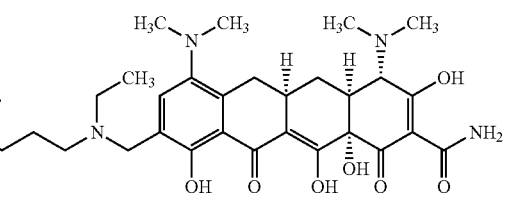
O
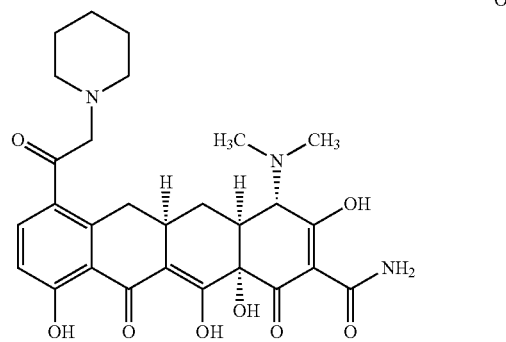
P
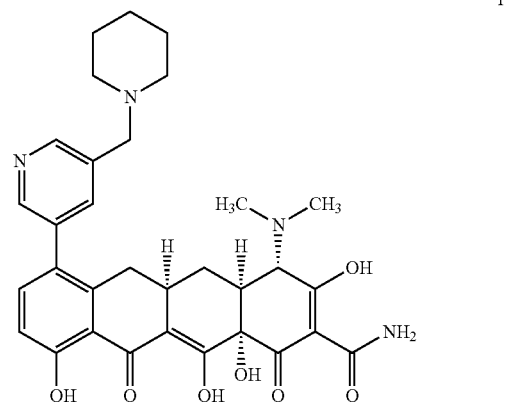
Q
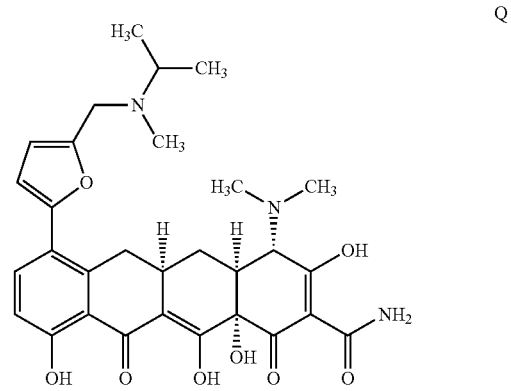
R
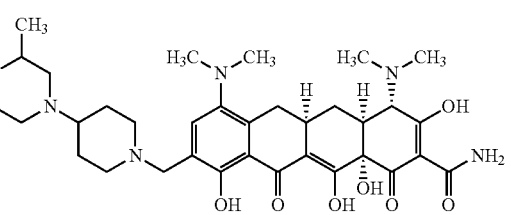

-continued
S
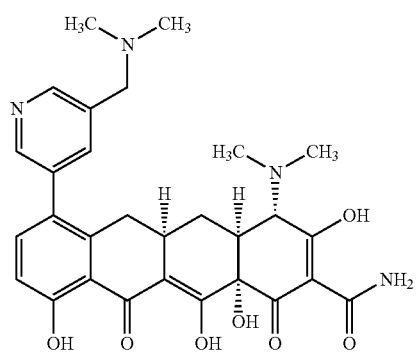
T
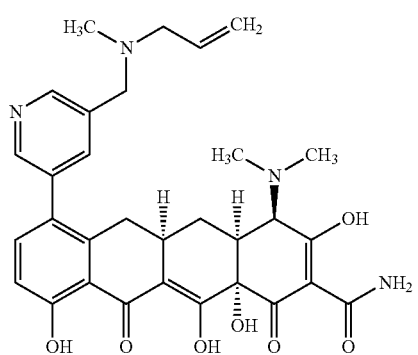
U
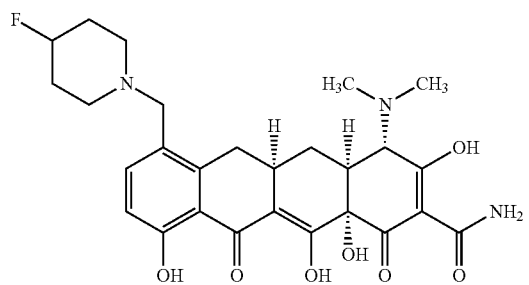
V
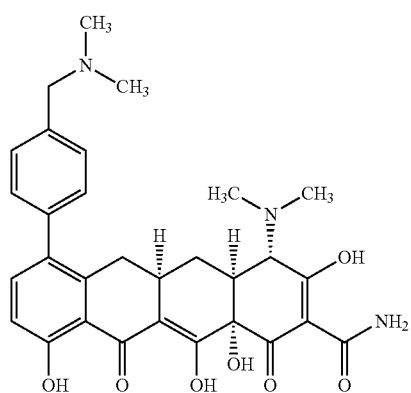
-continued
W
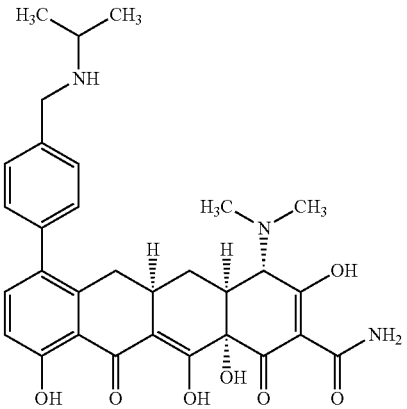
X
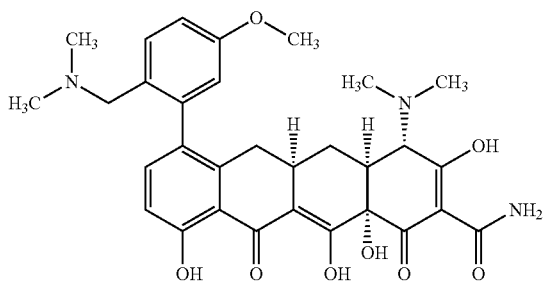
Y
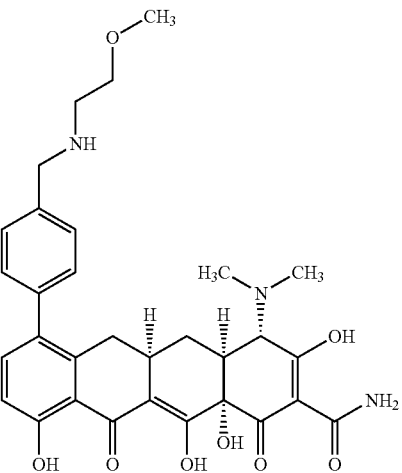
Z
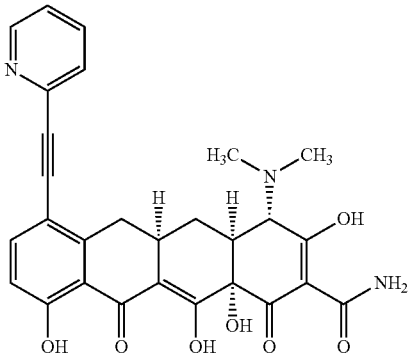

AA
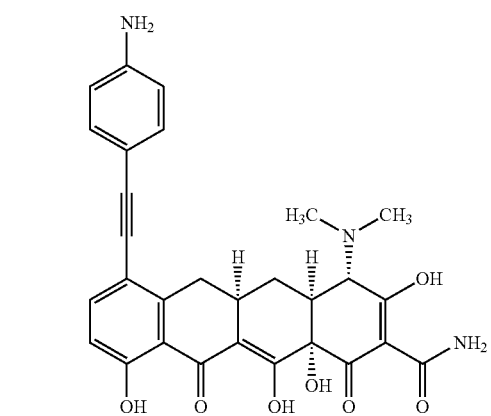
AB
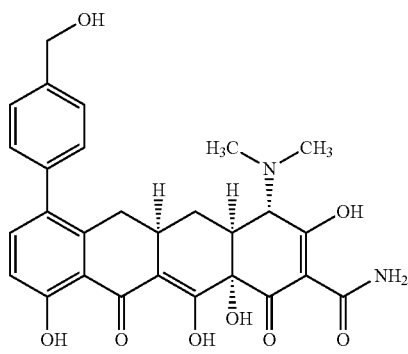
AC
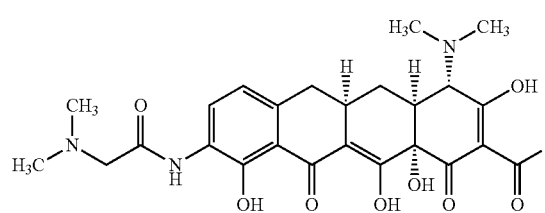
AD
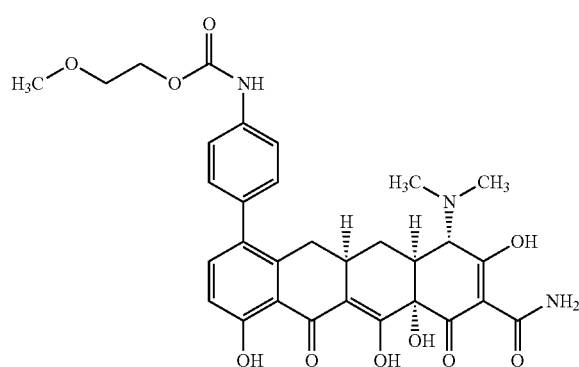
AE
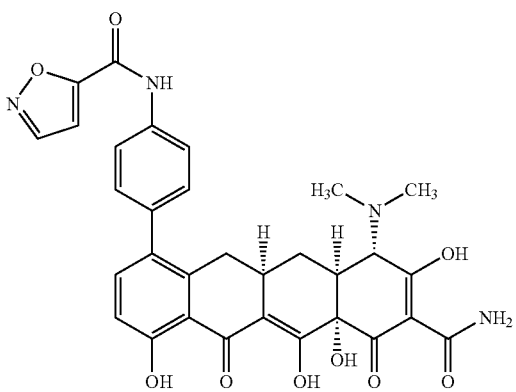
AF
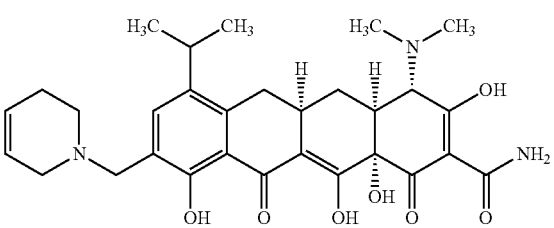
AG
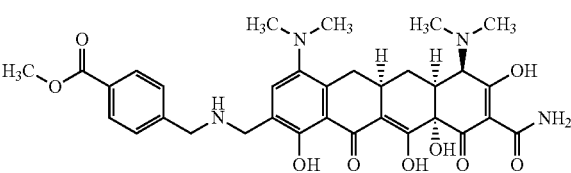
AH
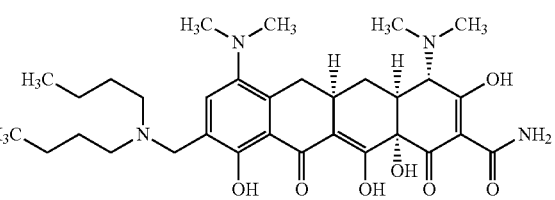
AI
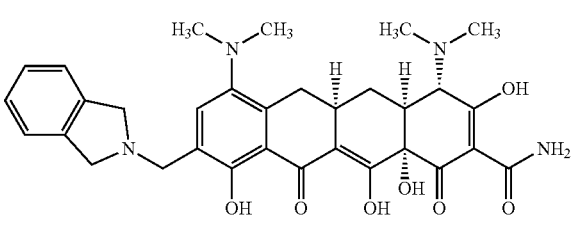

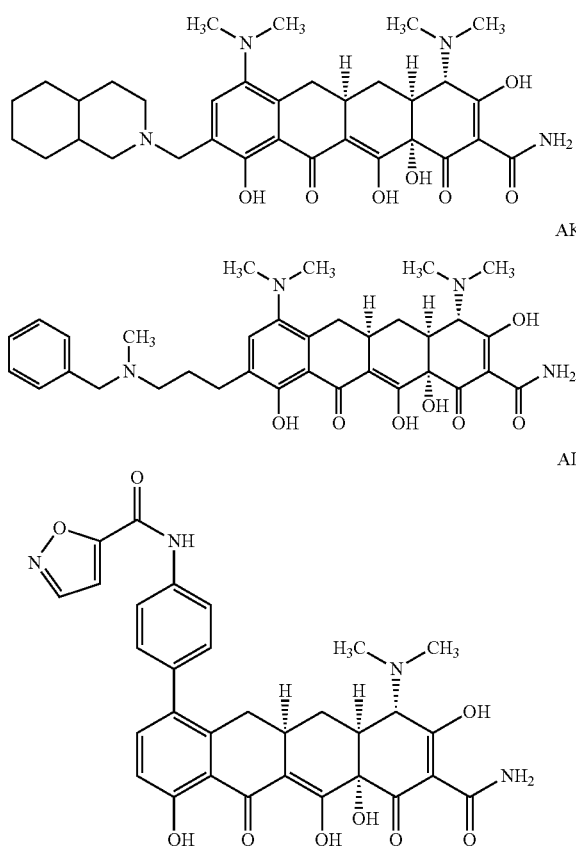

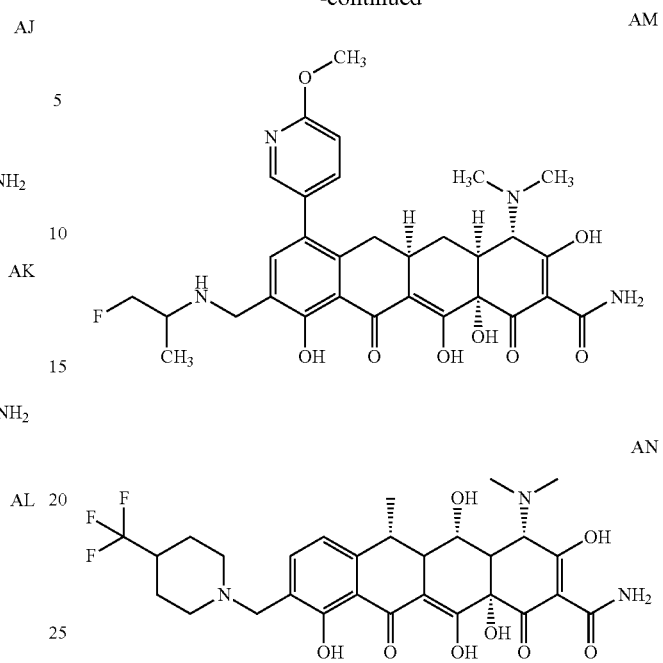

and pharmaceutically acceptable salts thereof.

The tetracycline compounds of this invention can be synthesized using the methods described in the Schemes and/or by other techniques known to those of ordinary skill in the art.

The substituted tetracycline compounds of the invention can be synthesized using the methods described in the following schemes and by using art recognized techniques. All novel substituted tetracycline compounds described herein are included in the invention as compounds.

SCHEME 1

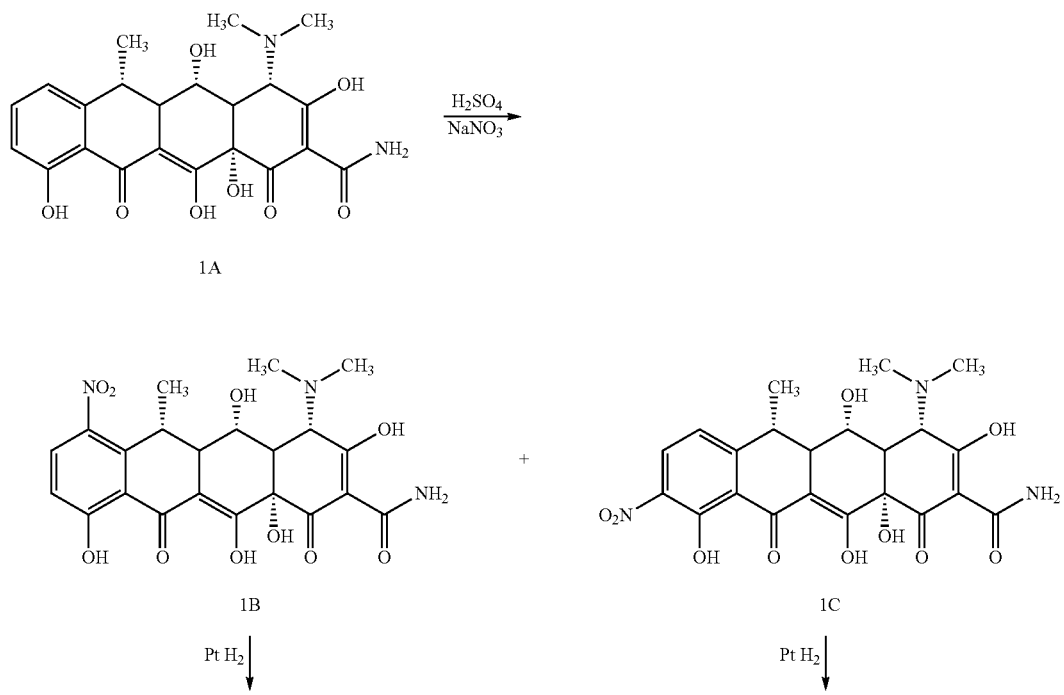

-continued

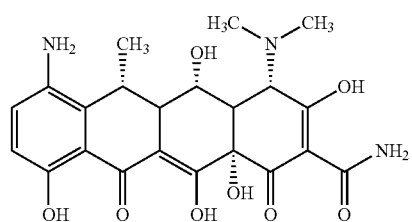
1D

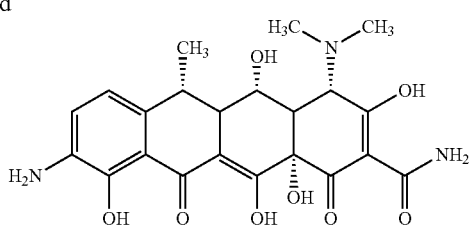
1E

↓ HONO

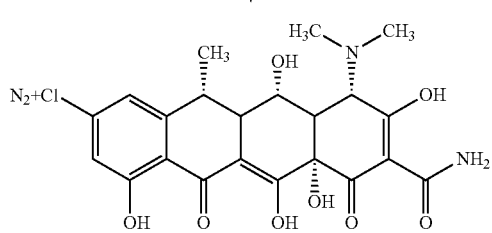
1F

↓ HONO

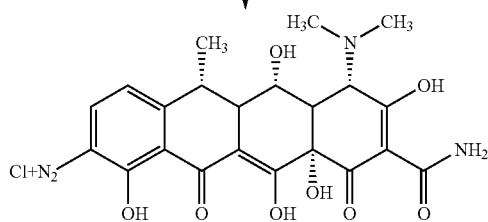
1G

↓

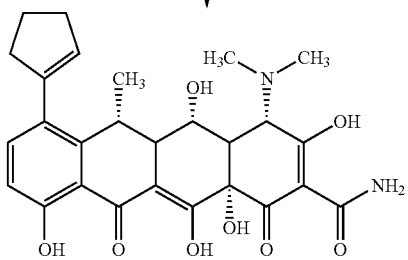
1H

↓

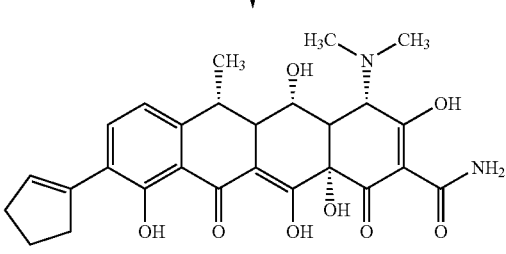
1I 9- and 7-substituted tetracyclines can be synthesized by the method shown in Scheme 1. As shown in Scheme 1, 9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate reactive reagent to yield the desired compound (e.g., in Scheme 1, 7-cyclopent-1-enyl doxycycline (1H) and 9-cyclopent-1-enyl doxycycline (1I)).

SCHEME 2

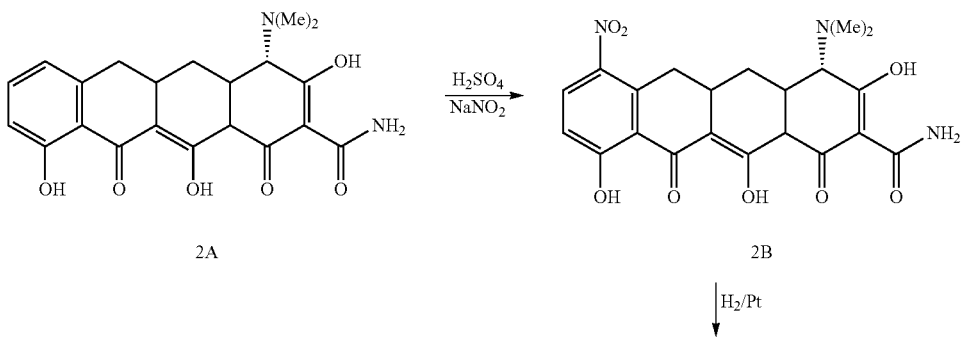

↓ H$_2$/Pt

-continued

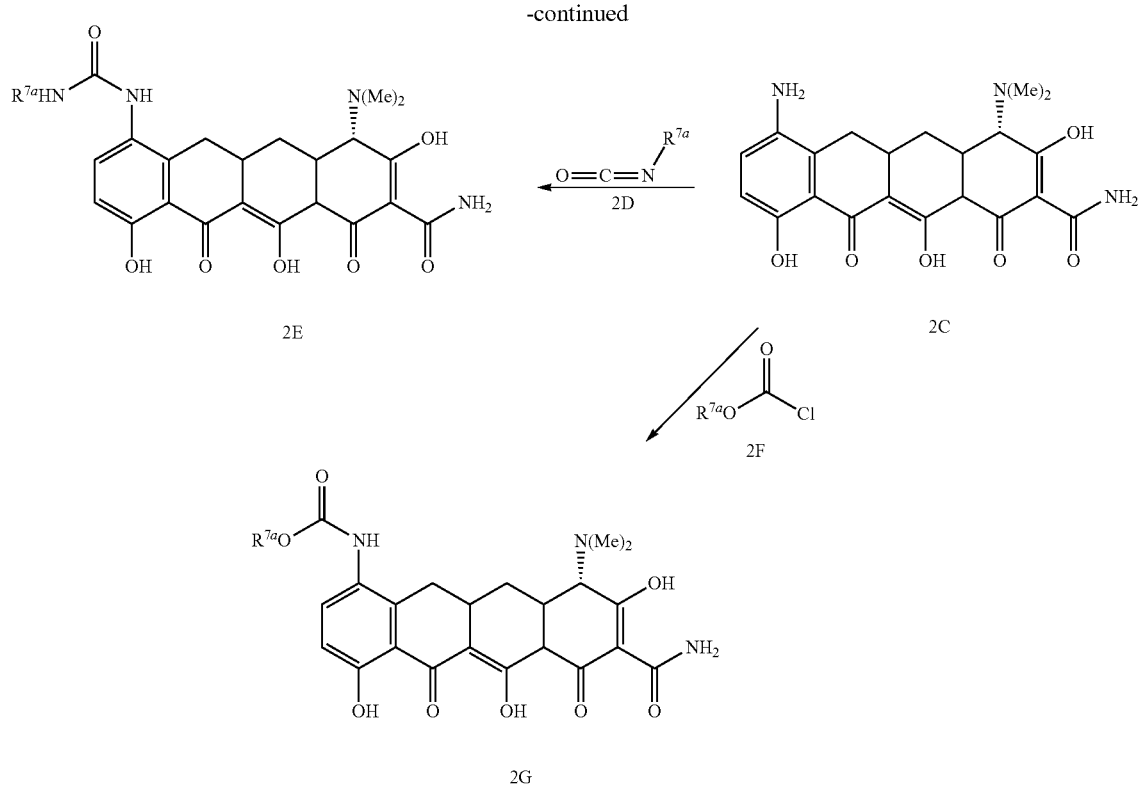

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

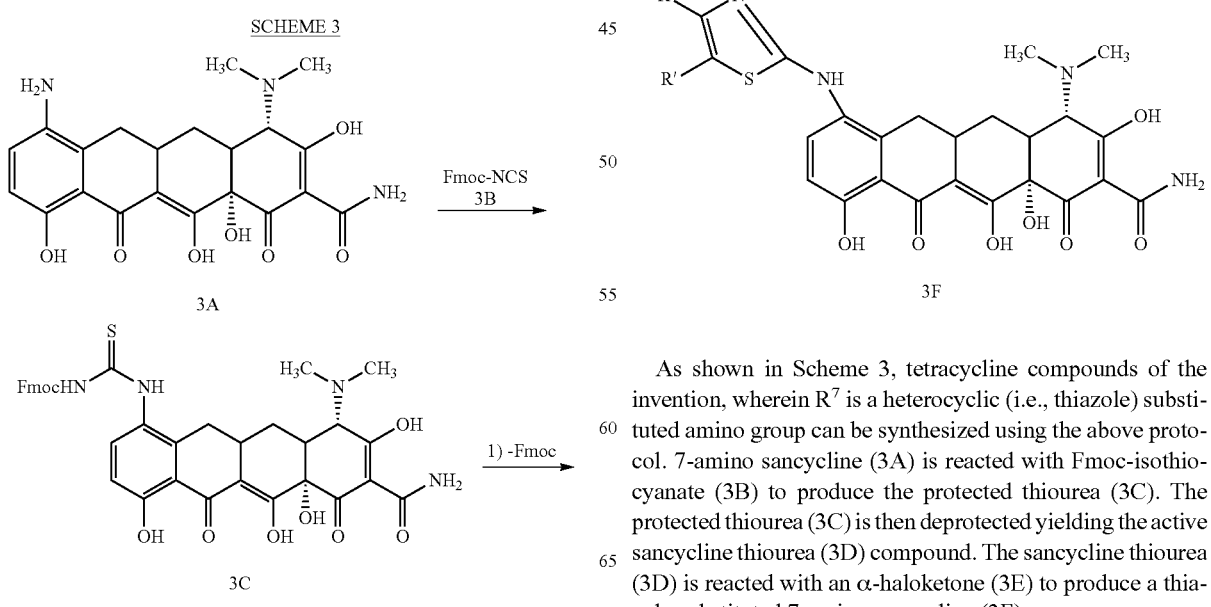

As shown in Scheme 3, tetracycline compounds of the invention, wherein $R^7$ is a heterocyclic (i.e., thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

SCHEME 4

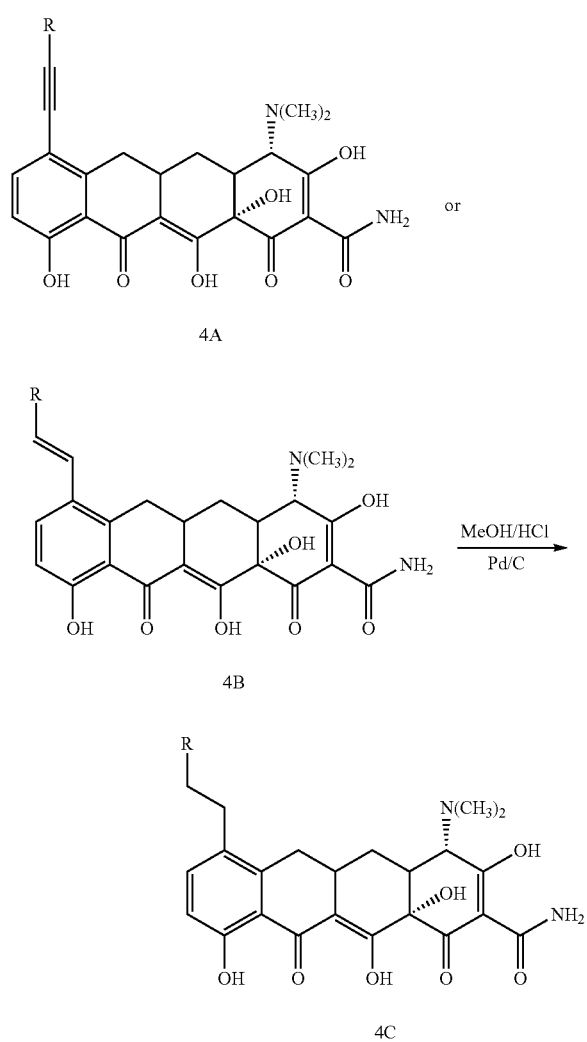

7-alkenyl tetracycline compounds, such as 7-alkynyl sancycline (4A) and 7-alkenyl sancycline (4B), can be hydrogenated to form 7-alkyl substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

SCHEME 5

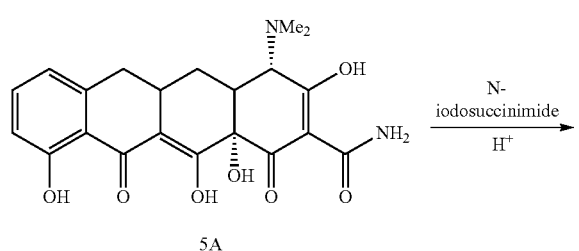

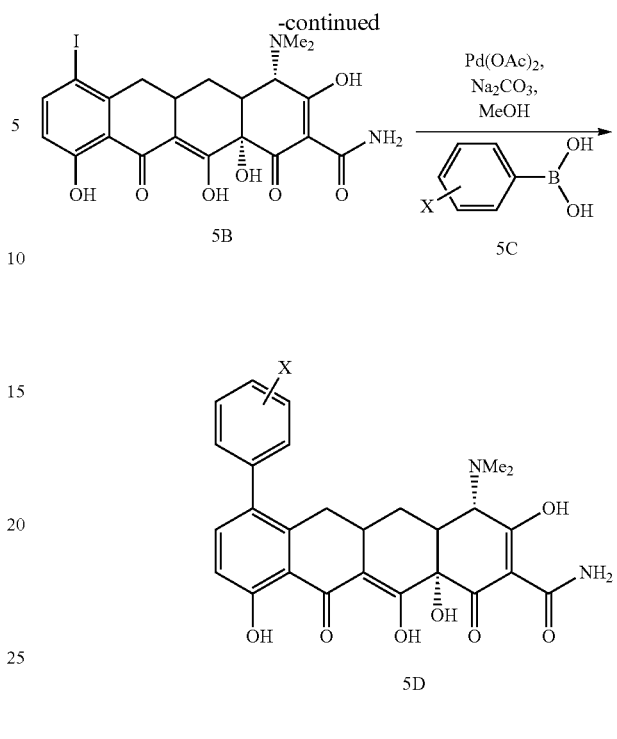

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions. The reaction is quenched, and the resulting 7-iodo sancycline (5B) can then be purified using standard techniques known in the art. To form the aryl derivative, 7-iodo sancycline (5B) is treated with an aqueous base (e.g., $Na_2CO_3$) and an appropriate boronic acid (5C) and under an inert atmosphere. The reaction is catalyzed with a palladium catalyst (e.g., Pd $(OAc)_2$). The product (5D) can be purified by methods known in the art (such as HPLC). Other 7-aryl, alkenyl, and alkynyl tetracycline compounds can be synthesized using similar protocols.

The 7-substituted tetracycline compounds of the invention can also be synthesized using Stille cross couplings. Stille cross couplings can be performed using an appropriate tin reagent (e.g., R—SnBu$_3$) and a halogenated tetracycline compound, (e.g., 7-iodosancycline). The tin reagent and the iodosancycline compound can be treated with a palladium catalyst (e.g., Pd(PPh$_3$)$_2$Cl$_2$ or Pd(AsPh$_3$)$_2$Cl$_2$) and, optionally, with an additional copper salt, e.g., CuI. The resulting compound can then be purified using techniques known in the art.

SCHEME 6

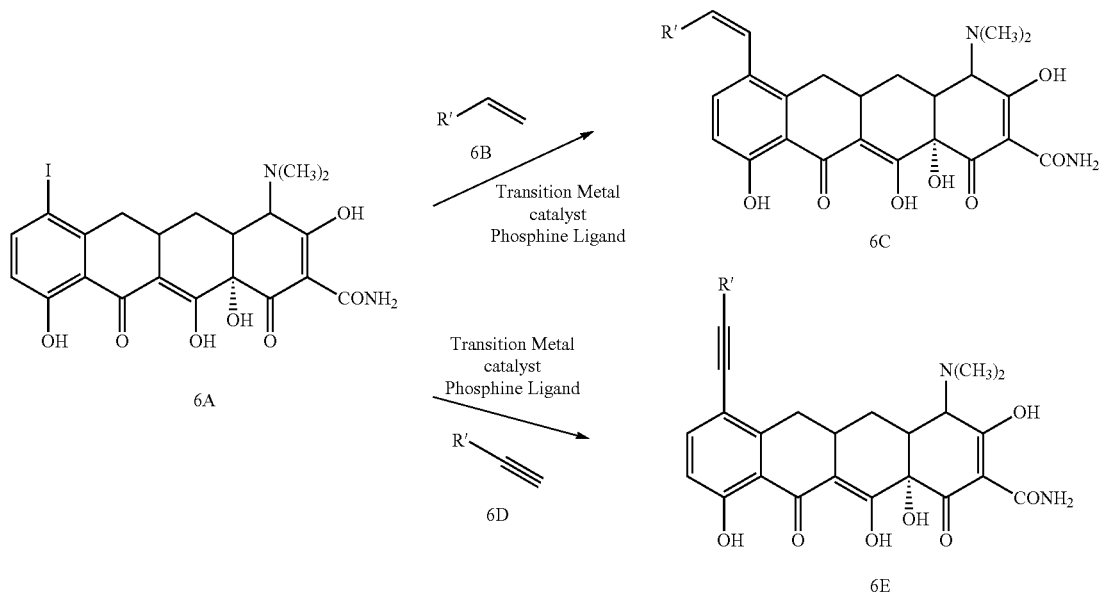

The compounds of the invention can also be synthesized using Heck-type cross coupling reactions. As shown in Scheme 6, Heck-type cross-couplings can be performed by suspending a halogenated tetracycline compound (e.g., 7-iodosancycline, 6A) and an appropriate palladium or other transition metal catalyst (e.g., Pd(OAc)$_2$ and CuI) in an appropriate solvent (e.g., degassed acetonitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E)tetracycline compound can then be purified using techniques known in the art.

SCHEME 7

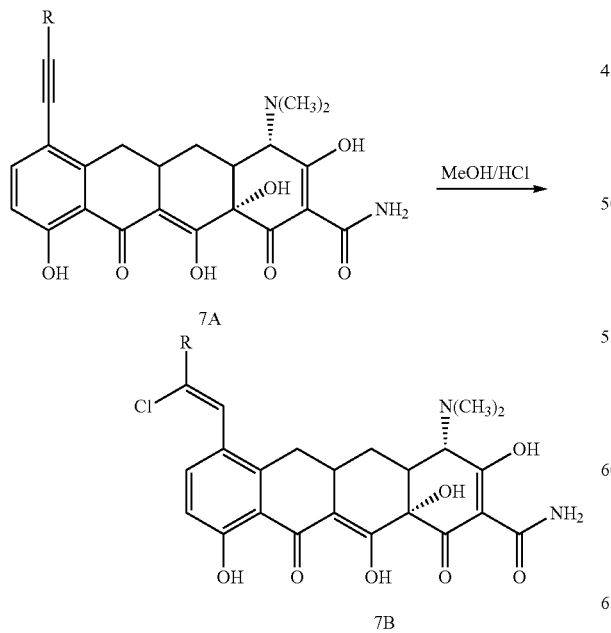

To prepare 7-(2'-chloro-alkenyl)-tetracycline compounds, the appropriate 7-(alkynyl)-sancycline (7A) is dissolved in saturated methanol and hydrochloric acid and stirred. The solvent is then removed to yield the product (7B).

SCHEME 8

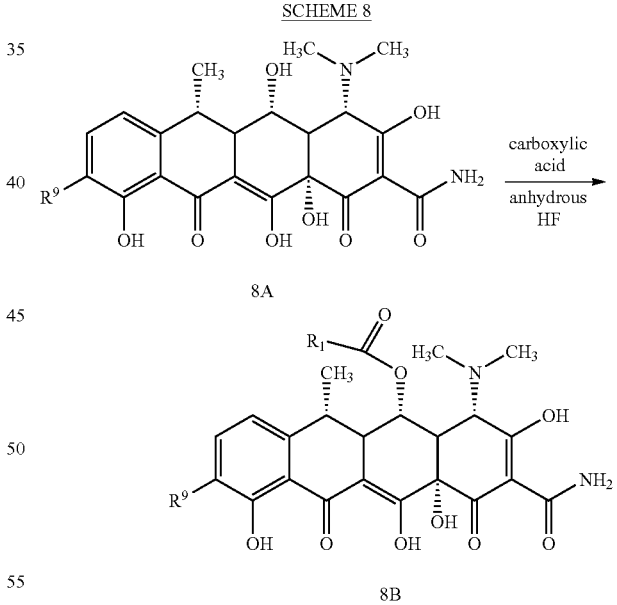

As depicted in Scheme 8, 5-esters of 9-substituted tetracycline compounds can be formed by dissolving the 9-substituted compounds (8A) in strong acid (e.g., HF, methanesulphonic acid, and trifluoromethanesulfonic acid) and adding the appropriate carboxylic acid to yield the corresponding esters (8B).

As shown in Scheme 9 below, 7 and 9 aminomethyl tetracyclines may be synthesized using reagents such as hydroxymethyl-carbamic acid benzyl ester.

SCHEME 9

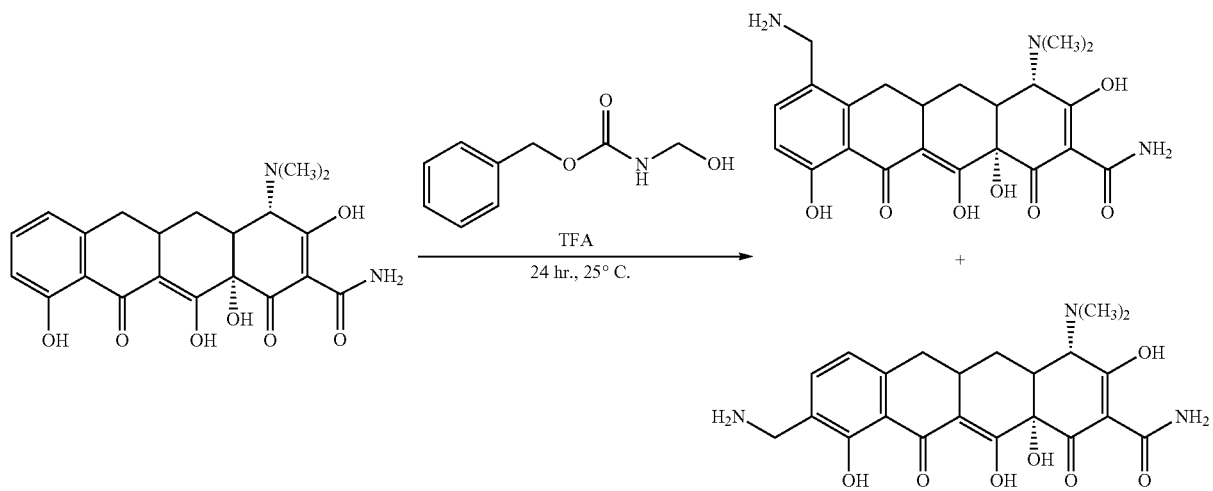

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl(benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls," the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl," "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group.

The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through nonadjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts," *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

In another further embodiment, the substituted tetracycline compound is administered in combination with a second agent.

The language "in combination with" a second agent includes co-administration of the tetracycline compound, and with the second agent, administration of the tetracycline compound first, followed by the second agent and administration of the second agent, followed by the tetracycline compound. The second agent may be any agent which is known in the art to treat, prevent, or reduce the symptoms of a *Bacillus anthracis* infection. Furthermore, the second agent may be any agent of benefit to the subject when administered in combination with the administration of an tetracycline compound.

Examples of second agents include antibiotics, such as rifampin, vancomycin, ampicillin, chloramphenicol, imipenem, clindamycin, and clarithromycin.

In another embodiment, the invention pertains to pharmaceutical compositions comprising an effective amount of a substituted tetracycline compound of the invention for the treatment of a *Bacillus anthracis* infection and a pharmaceutically acceptable carrier.

The language "pharmaceutically acceptable carrier" includes substances capable of being coadministered with the tetracycline compound(s), and which allow both to perform their intended function, e.g., treat or prevent a *Bacillus anthracis* infection. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays (e.g., aerosols, etc.), creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The compositions of the invention may be formulated such that the tetracycline compositions are released over a period of time after administration.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g., for treatment of livestock such as cattle, sheep, goats, cows, swine and the like; poultry such as chickens, ducks, geese, turkeys and the like; horses; and pets such as dogs and cats.

It will be appreciated that the actual preferred amounts of active compounds used in a given therapy will vary according to the specific compound being used, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a substituted tetracycline of the invention, for the preparation of a medicament. The medicament may include a pharmaceutically acceptable carrier and the tetracycline compound is an effective amount, e.g., an effective amount to treat a *Bacillus anthracis* infection.

EXEMPLIFICATION OF THE INVENTION

Example 1

Antibacterial Activity of Tetracycline Compounds Against Susceptible and (Multiple) Antibiotic Resistant Organisms Efflux. The tetracycline efflux proteins, in general, confer resistance to both tetracycline and doxycycline. *S. aureus* RN4250 bears a TetK efflux mechanism and is resistant to both agents, but susceptible to minocycline (Table 2). A number of tetracyclines that overcome gram-positive efflux (Table 2) have been identified.

TABLE 2

MICs (μg/ml) of novel TCs against strains with efflux resistance determinants.

| | MIC (ug/ml) | |
|---|---|---|
| Compound | S. aureus RN450 [a] | S. aureus RN4250 [b] |
| Doxycycline | 0.06 | 4 |
| Minocycline | 0.25 | 0.5 |
| Tetracycline | 0.06 | 64 |
| O | 0.06 | 0.06 |
| M | 0.06 | 0.06 |
| Q | 0.06 | 0.06 |
| P | 0.06 | 0.06 |
| S | 0.06 | 0.06 |
| T | 0.06 | 0.06 |
| U | 0.06 | 0.06 |
| V | 0.06 | 0.06 |
| W | 0.06 | 0.06 |
| X | 0.06 | 0.06 |
| Y | 0.06 | 0.06 |

[a] Wild type *S. aureus*.
[b] Contains a TetK (efflux) resistance determinant.

Ribosome protection. The ribosome protection determinants, which confer resistance to tetracycline, doxycycline and minocycline, are predominantly found in gram-positive bacteria and are probably the most widespread tetracycline resistance determinant in these organisms. A number of tetracycline compounds that can overcome this mechanism of resistance in a variety of gram-positive bacteria including *S. aureus*, *E. faecium*, and *S. pneumoniae* (Table 3).

TABLE 3

MICs (μg/ml) of tetracycline compounds against strains with ribosome protection resistance determinants

| | MIC (ug/ml) | | | | |
|---|---|---|---|---|---|
| Compound | S. aureus RN450 [a] | S. aureus MRSA5 [b] | E. faecium 494 [c] | S. pneumoniae 157E [a] | S. pneumoniae 700905 [d] |
| Doxycycline | 0.06 | 4 | 8 | 0.06 | 4 |
| Minocycline | 0.25 | 2 | 16 | 0.06 | 8 |

TABLE 3-continued

MICs (μg/ml) of tetracycline compounds against
strains with ribosome protection resistance determinants

| | MIC (ug/ml) | | | | |
|---|---|---|---|---|---|
| Compound | S. aureus RN450 [a] | S. aureus MRSA5 [b] | E. faecium 494 [c] | S. pneumoniae 157E [a] | S. pneumoniae 700905 [d] |
| Tetracycline | 0.06 | 32 | 64 | 0.06 | 32 |
| Z | 0.13 | 0.5 | 2 | 0.06 | ND [e] |
| AA | 1 | 0.5 | 1 | 0.5 | 1 |
| AB | 0.06 | 1 | 0.06 | 0.06 | 4 |
| AD | 0.06 | 1 | 2 | 0.13 | 0.5 |
| AE | 0.06 | 0.5 | 2 | 0.13 | 1 |
| AK | 1 | 2 | 1 | 0.5 | 0.5 |

[a] Wild type.
[b] Methicillin resistant S. aureus; contains TetM (ribosome protection); also multi-drug resistant.
[c] Contains TetL (efflux) and TetM (ribosome protection); is also resistant to vancomycin and erythromycin.
[d] Contains TetM (ribosome protection); is also resistant to penicillin and erythromycin.
[e] ND, not determined.

Efflux and ribosome protection concurrently. A number of tetracycline compounds were tested against gram-positive bacteria possessing both tetracycline efflux and ribosome protection determinants as well as other non-tetracycline resistance mechanisms. Compounds with substitutions at both $R^7$ and $R^9$ position in Formula I e.g., substituted 7-dimethylamino-9-aminomethylcyclines and 7-aryl or heteroaryl sancyclines) demonstrated activity against both tetracycline sensitive isolates and tetracycline resistant gram-positive bacteria containing efflux and ribosome protection determinants (Table 4).

TABLE 4

MICs (μg/ml) of tetracycline compounds against
strains with ribosome protection and efflux resistance determinants.

| | MIC (ug/ml) | | | |
|---|---|---|---|---|
| Compound | E. faecium 494 [a] | E. faecalis 29212 [b] | S. aureus MRSA5 [c] | S. pneumoniae 700905 [d] |
| Doxycycline | 16 | 4 | 4 | 4 |
| Minocycline | 16 | 4 | 2 | 8 |
| Tetracycline | 64 | 16 | 32 | 32 |
| A | 1 | 1 | 1 | 0.25 |
| B | 1 | 1 | 1 | 0.5 |
| C | 0.25 | 0.5 | 1 | 0.25 |
| D | 1 | 0.25 | 1 | 0.25 |
| E | 1 | 0.25 | 0.25 | 0.06 |
| F | 1 | 0.5 | 0.5 | 0.25 |
| G | 1 | 0.5 | 0.5 | 0.06 |
| H | 0.5 | 0.5 | 0.35 | 0.06 |
| I | 1 | 1 | 1 | 0.5 |
| J | 1 | 0.25 | 0.5 | 0.06 |
| K | 1 | 1 | 0.5 | 0.25 |
| L | 1 | 1 | 0.5 | 0.75 |
| R | 1 | 2 | 1 | 0.13 |
| N | 0.5 | 1 | 1 | 0.13 |
| AH | 0.25 | 0.25 | 1 | 0.06 |

[a] Has TetM (ribosome protection) and TetL (efflux); is resistant to vancomycin and erythromycin.
[b] Has TetM (ribosome protection).
[c] Methicillin resistant S. aureus; contains TetM, ribosome protection; also multi-drug resistant.
[d] Has TetM (ribosome protection).

*Bacillus cereus.* In order to prevent the unnecessary use of the anthrax pathogen, a group of tetracycline resistant *B. cereus* was obtained. In this panel, *B. cereus* 95/3032 and 98/2658 were classified as tetracycline susceptible whereas *B. cereus* 98/2620 and 97/4144 were tetracycline resistant (Table 6). Preliminary MICs were determined for common antibiotics against the *B. cereus* isolates (Table 5).

*B. cereus* containing natural tetracycline resistance determinants were chosen rather than creating isogenic tetracycline resistant *B. anthracis* strains since it would be a violation of International Bioweapons Treaty to purposefully create an antibiotic resistant category A agent. In addition, *B. cereus* are generally more tetracycline resistant than *B. anthracis.*

TABLE 5

Activity of tetracycline compounds against
tetracycline susceptible and tetracycline resistant *Bacillus cereus.*

| | MIC (ug/ml) | | | |
|---|---|---|---|---|
| Compound | B. cereus 98/2620 [a] | B. cereus 95/3032 [b] | B. cereus 98/2658 [c] | B. cereus 97/4144 [d] |
| Doxycycline | 4 | ≦0.06 | ≦0.06 | 4 |
| Minocycline | 0.5 | ≦0.06 | ≦0.06 | 0.5 |
| Tetracycline | 32 | ≦0.06 | ≦0.06 | 64 |
| Cefotaxime | 64 | >64 | >64 | 32 |
| Penicillin | 32 | >64 | >64 | >64 |
| Vancomycin | 1 | 1 | 2 | 1 |
| Erythromycin | 0.06 | 0.125 | 1 | 0.125 |
| Clindamycin | 0.25 | 0.5 | 0.5 | 0.5 |

[a] An industrial fermenter isolate, serotype 1.
[b] Isolated from an orthopedic-related area, serotype 24.
[c] Non-typeable.
[d] Isolated from an individual with food poisoning, serotype AA.

*Bacillus anthracis.* The panel of *B. anthracis* isolates (n=27) that was available for susceptibility studies included two organisms that exhibit reduced susceptibility to doxycycline (Table 6). *B. anthracis* V770 was 4→33-fold less susceptible to doxycycline than 25 other *B. anthracis* and strain V770NPIR was fully doxycycline-resistant.

The group of organisms listed in Table 6 all possessed the same tetracycline resistance determinants that would be found in *B. anthracis* and the majority were multi-drug resistant. The criteria for selecting compounds for subsequent testing in *B. anthracis* were (a) the compounds must not possess cytotoxicity in vitro (Table 9) and (b) the compounds were required to possess a MIC of ≦0.5 μg/ml against this panel of resistant isolates (Table 7). At least five tetracycline compounds were identified (Table 7).

The activities of these tetracyclines were tested against *B. anthracis* (n=5), including the tetracycline resistant strains V770 and V770NPIR (Table 7). As illustrated, these compounds possessed exceptional activity against tetracycline susceptible and resistant *B. anthracis* isolates in vitro (Table 7). Compounds AI, H, and AJ all contain substituents at the $R^9$ position of the tetracycline core while compounds AM and AF bear substitutions at the $R^7$ and $R^9$ positions. Without being bound by theory, these data support the hypothesis that tetracycline compounds directed against common tetracycline resistant organisms, e.g., *S. aureus*, *S. pneumoniae*, and *Enterococcus* spp. may also target tetracycline resistant *B. anthracis.*

TABLE 6

Activity of tetracycline compounds against
susceptible and doxycycline resistant *B. anthracis.*

| | MIC (ug/ml) | | | | |
|---|---|---|---|---|---|
| Compound | Vollum1B | Sterne | Ame | V770 | V770NPIR |
| Ciprofloxacin | 0.25 | 0.25 | 0.25 | 0.12 | 0.25 |
| Doxycycline [a] | 0.06 | 0.12 | <0.03 | 1 | 32 |
| AI | <0.03 | <0.03 | 0.06 | 0.12 | 0.06 |

TABLE 6-continued

Activity of tetracycline compounds against susceptible and doxycycline resistant *B. anthracis*.

| Compound | MIC (ug/ml) Vollum1B | Sterne | Ame | V770 | V770NPIR |
|---|---|---|---|---|---|
| AM | 0.06 | 0.06 | 0.06 | 0.12 | 0.06 |
| AF | <0.03 | <0.03 | <0.03 | 0.06 | 0.06 |
| H | <0.03 | <0.03 | <0.03 | <0.03 | 0.06 |
| AJ | <0.03 | <0.03 | <0.03 | <0.03 | <0.03 |

[a] The activity of doxycycline against the entire *B. anthracis* panel (n = 27) is as follows: MIC50 = 0.06 μg/ml; MIC90 = 0.25 μg/ml; MIC Range =< 0.03-32 μg/ml.

TABLE 7

Activity of tetracycline compounds against common susceptible and tetracycline resistant bacteria.

| Compound | MIC (ug/ml) *S. aureus* MRSA5 [a] | *E. faecium* 494 [b] | *E. faecalis* 29212 [c] | *S. pneumoniae* 700905 [d] |
|---|---|---|---|---|
| Doxycycline | 4 | 16 | 4 | 4 |
| Minocycline | 2 | 16 | 4 | 8 |
| Tetracycline | 32 | 64 | 16 | 32 |
| Al | 0.5 | 0.5 | 0.5 | 0.06 |
| AM | 0.25 | 0.25 | 0.13 | 0.06 |
| AF | 0.13 | 0.25 | 0.13 | 0.06 |
| H | 0.35 | 0.5 | 0.5 | 0.06 |
| AJ | 0.5 | 0.5 | 0.5 | 0.06 |

[a] Methicillin resistant *S. aureus*; contains TetM, ribosome protection; also multi-drug resistant.
[b] Has TetM (ribosome protection) and TetL (efflux); is resistant to vancomycin and erythromycin.
[c] Has TetM (ribosome protection).
[d] Has TetM (ribosome protection); is resistant to penicillin and erythromycin.

Example 2

Additional Potential Mechanisms of Antibacterial Activity by Tetracycline Compounds In addition to inhibiting protein synthesis, molecules within the tetracycline family are reported to affect peptidoglycan biosynthesis. Using cell-free macromolecular synthesis assays early studies divided the tetracycline compounds into two classes based on these additional activities. Class 1 compounds (tetracycline, minocycline, and doxycycline) were potent inhibitors of protein synthesis compared to the weak effects of class 2 molecules (chelocardin, anhydrotetracycline, and 4-epi-anhydrochlorotet).

Using chemical footprinting assays, minocycline, doxycycline, and tetracycline were shown to affect the reactivity of nucleotides known to mediate binding of the antibiotics within the 16S rRNA. Tigecycline exhibited a chemical footprint similar to that of tetracycline. A similar effect was not seen with chelocardin or anhydrotetracycline, which correlates with their poor activity against the purified ribosome in vitro.

As illustrated in Table 8, these previous findings were confirmed and methods for deriving IC50 values (i.e., compound concentration necessary to inhibit a biological process by 50%) were developed. In particular, compounds AA, O, and tigecycline have a profile similar to class I compounds. Compounds AA and A also affect peptidoglycan biosynthesis.

TABLE 8

Effect of tetracycline compounds on macromolecular synthesis of *S. aureus* RN450.

| Antibiotic | MIC (μg/ml) | Protein synthesis [a] IC50 | IC90 | Peptidoglycan synthesis IC50 | IC90 |
|---|---|---|---|---|---|
| Tetracycline | 0.06 | <0.03 | 0.11 | >32 | >32 |
| Minocycline | 0.19 | <0.03 | 0.1 | 4.6 | 20.9 |
| Doxycycline | 0.06 | <0.03 | <0.03 | 3.9 | 18.23 |
| Anhydro-tetracycline | 2 | <0.03 | <0.03 | 19.2 | >32 |
| Tigecycline | 2 | 0.12 | 0.68 | >32 | >32 |
| AA | 1 | 0.14 | 1.4 | 3.8 | 23 |
| AB | 0.06 | 0.19 | 1.8 | 18.3 | >32 |
| A | 0.25 | 1.9 | 5 | 2.1 | 3.8 |
| AE | 0.06 | 0.07 | 0.62 | 6.0 | >32 |
| O | 0.06 | 0.33 | 0.92 | >32 | >32 |

[a] Compounds were assayed against *S. aureus* RN450, a TC susceptible organism and IC50 and IC90 values are reported in μg/ml.

Example 3

In Vitro and In Vivo Toxicity

An in vitro determination of the cytotoxicity of the compounds of the invention was performed using standard mammalian cell assays and in vivo using mice. Specifically, African green monkey kidney (COS-1) and Chinese hamster ovary (CHO-K1) cell lines were used according to standard methods (see Zhi-Jun, Y., N. Sriranganathan, T. Vaught, S. K. Arastu, and S. A. Ahmed. 1997. A dye-based lymphocyte proliferation assay that permits multiple immunological analyses: mRNA, cytogenetic, apoptosis, and immunophenotyping studies. *J Immunol Methods* 210:25-39). Briefly, suspensions of tissue culture cells were grown overnight in the presence of serial dilutions of drug up to a maximum concentration of 50 or 100 μg/ml. The metabolism of the tissue culture cells was monitored with resazurin, a soluble non-toxic dye. Control cytotoxic and non-cytotoxic compounds were routinely included in all assays. Tox100 values represented the concentration of compound necessary to inhibit cellular proliferation by 100%. Compounds without measurable cytotoxicity in vitro were assigned a Tox100 value of greater than the highest concentration assayed (e.g., 50 or 100 μg/ml). The results are shown in Table 9.

TABLE 9

Cytotoxicity of tetracycline compounds.

| Compound | Tox50 (μg/ml) [a] COS-1 | CHO-K1 |
|---|---|---|
| AI | >100 | >100 |
| AM | >100 | 92.85 |
| AF | >100 | >100 |
| H | >100 | >100 |
| AJ | >100 | >100 |

[a] Represents the concentration necessary to cause 50% inhibition of cell growth in tissue culture cells.

Example 4

Efficacy of Tetracycline Compounds Against Susceptible and Resistant Organisms in Animal Infection Models In vivo efficacy as well as oral bioavailability of the tetracycline compounds were assessed in murine models of infection and compared to control tetracyclines and other currently available antibiotics. In the standard screening assay of acute systemic infection (Table 10), mice were given a lethal intraperitoneal inoculum of *S. pneumoniae* strain 157E (tetracycline susceptible) or 700905 (tetracycline resistant), followed by a single dose of drug, and then observed for survival over 48 hours. Each experiment routinely included an untreated group (n=5; expected survival<5%) and a group (n=5) treated with a conventional antibiotic (e.g., minocycline, ciprofloxacin, and ampicillin; expected survival>80%). The results are tabulated in Table 10.

TABLE 10

Efficacy of selected tetracyclines in the screening assay of acute systemic infection due to *S. pneumoniae* 157E.

| | SC | | PO | |
|---|---|---|---|---|
| Compound | dose | % survival | dose | % survival |
| B | 5 mg/kg | 100% | 5 mg/kg | 40% |
| C | 5 mg/kg | 100% | 10 mg/kg | 60% |
| D | 5 mg/kg | 0% | 10 mg/kg | 0% |
| AI | 5 mg/kg | 40% | 10 mg/kg | 0% |
| E | 5 mg/kg | 40% | 10 mg/kg | 0% |
| AM | 5 mg/kg | 100% | 50 mg/kg | 0% |
| F | 5 mg/kg | 100% | 50 mg/kg | 100% |
| AJ | 5 mg/kg | 100% | 50 mg/kg | 80% |

ND, not determined.

Compounds providing≧60% survival at 10 mg/kg were further assessed in a dose response study to determine the PD50 (the drug concentration necessary to prevent death in 50% of the mice in a treatment group). These experiments involved an untreated group, a group treated with a control antibiotic (e.g., minocycline, ciprofloxacin, and ampicillin), and up to five groups each receiving a different doses of an active experimental compound; all groups included 5 animals (Table 11). Compounds B and C were efficacious following tetracycline administration and compounds H and I exhibited oral activity (Tables 10 and 11). Compound H, which exhibited potentcy against tetracycline resistant *B. anthracis* (Table 6), exhibits IV and PO efficacy against infections caused by tetracycline susceptible and resistant organisms (Table 11), and is efficacious in a model of lung infection following IV and PO drug administration (Table 12).

TABLE 11

Efficacy (PD50) of selected tetracycline compounds in mice with acute systemic infection due to *S. pneumoniae*.

| | PD50 (mg/kg) | | | |
|---|---|---|---|---|
| | *S. pneumoniae* 157E | | *S. pneumoniae* 700905 | |
| Compound | IV | PO | IV | PO |
| Minocycline | 0.53 | 1.5 | >50 | >50 |
| Ciprofloxacin | >50 | ND | ND | >50 |
| Ampicillin | 0.6 | 1.1 | 43.7 | >50 |
| H | 1.1 | 5 | 2.2 | 12.7 |
| I | 1 | 13.4 | 2.2 | 31.6 |
| AN | 0.54 | 2.3 | 1.4 | 8.4 |

A chronic model of murine *S. pneumoniae* lung infection was also established and the efficacy of a variety of currently available tetracycline compounds were tested in this model (Table 12).

TABLE 12

Efficacy (PD50) of tetracycline compounds in mice with acute pulmonary infection due to *S. pneumoniae* PBS1339.

| | PD50 (mg/kg) | |
|---|---|---|
| Compound | IV | PO |
| Minocycline | 4.5 | 3.6 |
| Doxycycline | 7.1 | 35.3 |
| Ampicillin | ND | 3.2 |
| H | <5.0 | 3.6 |

Example 5

In Vivo Murine Model of *B. anthracis* Infection

In this example, mice were exposed to *B. anthracis* using whole body aerosol challenge, which approximated the mode of pathogen dissemination that would be expected during a bioterrorist event and was therefore preferred over other models (e.g., intratracheal inoculation). Animals were challenged with 75-100 LD50 of *B. anthracis* Ames strain spores (LD50 3.4×104 CFU/ml), which has been demonstrated repeatedly to cause death in 90-100% of untreated animals. Treatment with the substituted tetracycline compounds of the invention began 24 hours after challenge and continued for 21 days. Due to the persistence of ungerminated anthrax spores in the lungs of challenged animals, a treatment duration of 21 days was used regardless of the antibiotic class. Antibiotics were administered by parenteral injection or oral administration. Treatment groups were followed for an additional 30 days after cessation of antibiotic treatment. In addition to monitoring survival in each treatment group, animals were sacrificed at selected time points to monitor microbiological burdens. Tissues, including brain, spleen, lungs, heart, and liver were excised and pathogens were enumerated using agar plates. Additionally, emergence of resistance was monitored by culturing organs on antibiotic containing media (usually at 3× the baseline MIC).

Individual treatment groups consisted of 15 animals and the study endpoint was death after infectious challenge. Ciprofloxacin (30 mg/kg, q12h) or doxycycline (at experimentally determined doses) was included as the active control in all experiments. Moribund animals exhibiting labored breathing, showing signs of paralysis, or that are unresponsive were humanely euthanized. Challenged survivors were humanely euthanized at the conclusion of the example.

Throughout the study the mice were observed three to four times daily and mortality was recorded with each inspection. All moribund mice were euthanized and the deaths were recorded as the day of sacrifice. All mice that died or were sacrificed had their lungs and spleens quantitatively cultured on drug-free and antibiotic supplemented agar (3×MIC) to determine the effect of the treatment regimen on the total and drug-resistant bacterial populations, respectively.

Twenty-four hours after the last dose was given, a group of surviving mice (n=5) were sacrificed and the lungs and spleens were aseptically harvested. The homogenized specimens were washed with saline to prevent drug carryover and bacteria were quantitatively cultured on drug-free and antibiotic-supplemented agar (3×MIC). The remaining animals were observed for survival for 14 days after the last dose of drug is given. Those that were alive after the 2-week observation period were sacrificed and their lungs and spleens were quantitatively cultured for total and drug-resistant populations. Portions of the homogenates were “heat shocked” for spore determination and bacterial load was determined by plating onto culture media and incubated at 36° C.

Differences in survival between treatment and control groups was assessed by the Fisher exact test and by survival analysis techniques (Kaplan-Meier analysis and Cox proportional hazards modeling). Differences in bacterial concentrations in the lungs were determined by Student's t-test or by ANOVA. A P value<0.05 is considered statistically significant.

The results of the in vivo assay indicate that untreated mice exposed to *B. anthracis* survived approximately 4 days, all mice treated with 10 mg/kg compound AN survived the entire 21 days and 75% of mice treated with 25 mg/kg of compound AN survived the entire 21 days.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method for treating a *bacillus anthracis* infection in a subject, comprising administering to said subject an effective amount of a substituted tetracycline compound, such that said *bacillus anthracis* infection in said subject is treated, wherein said substituted tetracycline compound is of the formula I:

wherein
R$^{2''}$ is C(=O)—NR$^2$R$^{2'}$;
R$^2$, R$^{2'}$, and R$^3$ are hydrogen;
R$^{4a}$ and R$^{4b}$ are each alkyl;
R$^{10}$, R$^{11}$, and R$^{12}$ are each hydrogen;
R$^4$ and R$^{4'}$ are each independently NR$^{4a}$R$^{4b}$ or hydrogen;
R$^5$ and R$^{5'}$ are each hydrogen;
R$^6$ and R$^{6'}$ are each hydrogen;
R$^7$ is hydrogen, dialkylamino, alkyl, aryl, heterocyclic, or alkyl-O—N=C—CR$^{7g}$R$^{7h}$, wherein R$^{7g}$ and R$^{7h}$ are each independently hydrogen or alkyl;
R$^8$ is hydrogen;
R$^9$ is of the formula:

wherein:
J$^5$ and J$^6$ are each independently hydrogen, alkyl, alkenyl, or linked to form a ring; and
J$^7$ and J$^8$ are each alkyl, halogen, or hydrogen; and
X is CR$^6$R$^{6'}$;
or a pharmaceutically acceptable salt, ester or enantiomer thereof.

2. The method of claim 1, wherein R$^7$ is substituted or unsubstituted heteroaryl.

3. The method of claim 2, wherein R$^7$ is substituted or unsubstituted pyrimidinyl, pyridinyl, or furanyl.

4. The method of claim 1, wherein R$^7$ is hydrogen.

5. The method of claim 1, wherein J$^7$ and J$^8$ are each hydrogen.

6. The method of claim 5, wherein J$^6$ is hydrogen.

7. The method of claim 5, wherein J$^5$ is substituted or unsubstituted alkyl.

8. The method of claim 7, wherein J$^5$ is propyl.

9. The method of claim 5, wherein J$^5$ and J$^6$ are linked to form a ring.

10. The method of claim 9, wherein J$^5$ and J$^6$ are linked to form a substituted or unsubstituted piperidinyl ring or fused ring.

11. The method of claim 10, wherein said fused ring is 2,3-dihydro-indole or decahydro-isoquinoline.

12. The method of claim 10, wherein said piperidinyl ring is substituted with one or more halogens or one or more heterocyclic groups.

13. The method of claim 1, wherein said substituted tetracycline compound is selected from the group consisting of:

-continued

14. The method of claim 1, wherein said substituted tetracycline compound is administered in combination with a second agent.

15. The method of claim 14, wherein said second agent is an antibiotic.

16. The method of claim 15, wherein said second agent is selected from the group consisting of rifampin, vancomycin, ampicillin, chloramphenicol, imipenem, clindamycin, and clarithromycin.

17. The method of claim 1, wherein said *bacillus anthracis* is multidrug resistant.

18. The method of claim 1, wherein $R^7$ is dimethylamino.

19. The method of claim 8, wherein $R^7$ is substituted or unsubstituted heteroaryl, dimethylamino, or hydrogen.

20. The method of claim 9, wherein $R^7$ is substituted or unsubstituted heteroaryl, dimethylamino, or hydrogen.

21. The method of claim 10, wherein $R^7$ is substituted or unsubstituted heteroaryl, dimethylamino, or hydrogen.

22. The method of claim 11, wherein $R^7$ is substituted or unsubstituted heteroaryl, dimethylamino, or hydrogen.

23. The method of claim 12, wherein $R^7$ is substituted or unsubstituted heteroaryl, dimethylamino, or hydrogen.

* * * * *